United States Patent [19]

Obraztsov

[11] Patent Number: 5,505,964
[45] Date of Patent: Apr. 9, 1996

[54] LIQUID CONTACT LENS

[75] Inventor: Nickolay Obraztsov, St. Petersburg, Russian Federation

[73] Assignee: Allergan, Inc., Irvine, Calif.

[21] Appl. No.: 321,284

[22] Filed: Oct. 11, 1994

[51] Int. Cl.$^6$ .................................................. A61K 9/00
[52] U.S. Cl. ........................ 424/489; 424/427; 424/429; 623/4; 623/5; 623/6
[58] Field of Search ................................. 424/489, 427, 424/429

[56] References Cited

U.S. PATENT DOCUMENTS

| | | | |
|---|---|---|---|
| 4,641,934 | 2/1987 | Freeman | 623/6 |
| 4,642,112 | 2/1987 | Freeman | 623/6 |
| 4,709,996 | 12/1987 | Michelson | 424/429 |
| 4,913,536 | 4/1990 | Barnea | 359/666 |
| 4,994,504 | 2/1991 | Goldenberg | 525/937 |
| 5,066,301 | 11/1991 | Wiley | 623/6 |
| 5,124,734 | 6/1992 | Barnea | 351/169 |
| 5,235,441 | 8/1993 | Georgaras et al. | 359/19 |

Primary Examiner—Thurman K. Page
Assistant Examiner—Pamela S. Webber
Attorney, Agent, or Firm—Frank J. Uxa

[57] ABSTRACT

Compositions useful to at least partially correct an effect of ametropia in a mammalian eye are disclosed. Such compositions comprise a plurality of particles sized and adapted to be placed in proximity to the outer surface of the cornea of a mammalian eye to at least partially correct an effect of ametropia in the mammalian eye. Each of the plurality of particles carries a complete hologram, preferably a complete hologram which holds all the information needed to at least partially correct the effect of ametropia in the mammalian eye. A particularly useful method of administering the plurality of particles to a mammalian eye is to use an additional component in an amount effective to act as a carrier for the plurality of particles. In one embodiment, this carrier component is an ophthalmically acceptable, aqueous-based liquid. Methods for using such compositions to at least partially correct an effect of ametropia in the mammalian eye, and methods for producing such compositions are also disclosed.

24 Claims, No Drawings

LIQUID CONTACT LENS

BACKGROUND OF THE INVENTION

The present invention relates to compositions which are useful to at least partially correct an effect of ametropia in a mammalian eye, to methods for at least partially correcting such an effect of ametropia, and to methods for producing such compositions. More particularly, the present invention relates to a plurality of holographic particles, which are preferably administered to the mammalian eye in combination with a carrier component, which are effective, when in proximity to the cornea of the eye, to at least partially correct an effect of ametropia in the eye.

Contact lenses are very effective in correcting effects of ametropia in the eye. Ametropia is a generic term which refers to any condition of imperfect refraction of the eyes, such as nearsightedness, farsightedness or astigmatism.

One disadvantage of conventional contact lenses, whether hard contact lenses or soft contact lenses, is that certain wearers at least perceive a degree of discomfort when the lenses are being worn. In addition, contact lenses can be difficult for certain people to insert in and remove from the eye. Further, conventional contact lenses, when removed from the eye, are susceptible to being misplaced or lost.

The use of holographic lenses has been suggested, for example, in conventional spectacles or glasses (Georgaras et al U.S. Pat. No. 5,235,441) and in a contact lens or implant lens (Freeman U.S. Pat. No. 4,641,934). In these previous embodiments, a single holographic element is used in the lens.

It would be advantageous to provide a system not requiring either conventional spectacles or contact lenses for correcting one or more effects of ametropia in a human or animal eye.

SUMMARY OF THE INVENTION

New systems for at least partially correcting an effect of ametropia in a mammalian eye have been discovered. The present systems take advantage of known technology which is effective to produce holographic lenses, while, at the same time, producing compositions which are new and useful and provide substantial benefits relative to conventional lenses used to correct effects of ametropia. The present compositions are preferably applied or administered to the eye in combination with a carrier component, such as a liquid carrier, for example, in the form of eye drops, so that previous problems with inserting or removing contact lenses are eliminated. In addition, there are no problems of caring for contact lenses. The present systems are effective to at least partially correct an effect of ametropia in a mammalian eye, are easy to use with little or no risk of irritation or damage to the eye and may be provided in a disposable and/or single use form. In addition, the present compositions can be easily and effectively customized so as to correct the particular effect of ametropia from which a specific mammalian eye suffers.

In one broad aspect of the present invention, new compositions are provided and comprise a plurality of particles sized and adapted to be placed in proximity to the outer surface of the cornea of a mammalian eye to at least partially correct an effect of ametropia in the eye. Each of the plurality of particles carries a complete hologram. As use herein, the term "complete hologram" means that each particle holds all the information required to function as a fully operable hologram. Preferably, each particle carries a complete hologram which holds all the information needed to at least partially correct an effect of ametropia in a mammalian eye.

The term "complete hologram" is illustrated as follows. A holographic lens is produced on a film of thin material. This film of thin material, for example, the size of a conventional contact lens or larger, includes a complete hologram in that if the film was placed in proximity to the outer surface of the cornea (of an eye in need of a correction which can be provided by the produced holographic lens), at least partial, preferably substantially complete, correction of an effect of ametropia in the eye would result. This film of thin material can be divided into relatively small pieces or particles, each of which also includes the same complete hologram as does the larger film.

The plurality of particles are preferably sized and adapted to be substantially non-irritating to the mammalian eye when located in proximity to the outer surface of the cornea of the mammalian eye. More preferably, the particles are sized and adapted to be substantially non-detectable to the feeling sense of the human or animal in whose eye the plurality of particles are located. Thus, aside from the correction of the effect of ametropia, the human or animal in whose eye the plurality of particles are placed, preferably has substantially no sensation that such particles are present.

In one particularly useful embodiment, the plurality of particles are adapted to be oriented when located in proximity to the outer surface of the cornea of the eye. This orientation is effective to increase the degree of correction of the effect of ametropia in the eye. Preferably, the plurality of particles are oriented in the eye relative to the light entering the mammalian eye. In other words, the light preferably impacts directly onto the hologram being carried by each piece or particle.

In one embodiment, the plurality of particles carries a charge, for example, a negative charge, sufficient to at least facilitate the orientation of the particles in the eye. The particles may be shaped or have a shape which is effective to at least facilitate such orientation.

The present compositions preferably further comprise an additional component, for example, an aqueous-based liquid which is ophthalmically acceptable, in an amount effective to act as a carrier for the plurality of particles or an ophthalmically acceptable solid which solubilizes over a period of time after being in contact with tear fluid present in the eye into which the composition is placed.

In one embodiment, the additional component includes a maintenance component in an amount effective to maintain the plurality of particles in proximity to the outer surface of the cornea of the mammalian eye for a longer period of time relative to a substantially identical composition without the maintenance component. The use of such a maintenance component is effective to maintain the ametropia effect correction caused by the presence of the plurality of particles for a longer period of time so that, for example, a longer interval of time can pass before additional composition must be introduced to the eye to maintain the correction. The maintenance component is preferably present in an amount so that at least one of the viscosity and surface tension of the composition is increased relative to the corresponding property or properties of the tear fluid present in the mammalian eye into which the composition is to be placed.

In another broad aspect of the present invention, methods for at least partially correcting an effect of ametropia in a mammalian eye are provided. Such methods comprise placing in proximity to the outer surface of the cornea of a mammalian eye a plurality of particles, each of which carries a complete hologram, in an amount effective to at least partially correct an effect of ametropia in the mammalian eye. The present compositions described herein are particularly useful in these methods.

The placing step is preferably repeated at least once, and more preferably as often as needed to provide the desired correction.

Methods for producing the present compositions are provided and are included within the scope of the present invention. Such production methods comprise forming a thin film of material carrying a complete hologram which holds all the information needed to at least partially correct an effect of ametropia in a mammalian eye. This thin film of material carrying the complete hologram is divided into a plurality of particles so that each of the plurality of particles carries the complete hologram.

Alternatively, such production methods comprise forming a thin film of material carrying a plurality of complete holograms each of which holds all the information needed to at least partially correct an effect of ametropia in a mammalian eye. This thin film of material carrying the plurality of complete holograms is divided into a plurality of particles so that each of the plurality of particles carries at least one, preferably only one, of the complete holograms.

In one particularly useful embodiment, at a time before, during or after the forming step, a sufficient charge is selectively placed on one portion, for example, on the back side, of the thin film of material so that each of the plurality of particles is charged to at least facilitate orienting the plurality of particles when the plurality of particles are in proximity to the outer surface of a cornea of a mammalian eye. In one embodiment, the dividing step is effective to yield a plurality of particles each of which has a shape effective to at least facilitate orienting the plurality of particles when the plurality of particles are in proximity to the outer surface of a cornea of a mammalian eye. Thus, the method of manufacturing the present plurality of particles can influence the orientation of the particles in the eye and the degree of vision correction achievable by the plurality of particles.

If desired, the plurality of particles can be formed (for example, by dividing a thin film of material as described herein) or can be provided prior to forming the complete holograms on the particles. In this instance, individual complete holograms are placed on the individual particles.

In a preferred embodiment, the present methods further comprise combining the plurality of particles with an additional component in an amount effective to act as a carrier for the particles. This additional component is as described elsewhere herein.

These and other aspects of the present invention are set forth in the following detailed description, examples and claims.

DETAILED DESCRIPTION OF THE INVENTION

The present compositions comprise a plurality of particles which are sized and adapted to be placed in proximity to the outer surface of the cornea of a mammalian, preferably human, eye. With the plurality of particles located in proximity to (near) the outer corneal surface of a mammalian eye, such particles are effective to at least partially correct an effect of ametropia in the eye. Each of the plurality of particles included in the present compositions carries a complete hologram. Preferably, the complete hologram holds all the information needed to at least partially correct the effect of ametropia in the eye on (or in) which the plurality of particles are (or are to be) located.

The plurality of particles are preferably sized and adapted to be substantially non-irritating to the mammalian eye, and more preferably substantially non-detectable to the feeling sense of the human or animal on (or in) whose eye the plurality of particles are located.

The plurality of particles are made of a material on which one or more holographic lenses can be placed. In addition, such material should be such that it can be cut, shredded or otherwise divided into relatively small particles, each of which carries a complete hologram. The dividing of the thin film of material carrying the complete hologram or holograms should be done so as to maintain the integrity of the holographic lenses or holograms on the particles. In addition, the material from which the plurality of particles is made should be ophthalmically acceptable or at least ophthalmically compatible so that no substantial irritation or damage is caused to the eye by the presence of the particles in proximity to the cornea. Examples of suitable materials include: glass, quartz, various polymeric materials and the like. Although the size of the particles may vary over a broad range, in one embodiment such particles have a maximum transverse dimension, that is a maximum straight line dimension, in the range of about 10 microns or less to about 1000 microns or more.

Such plurality of particles are preferably formed to correct a specific effect of ametropia. Thus, each individual patient has his or her eyes examined for ametropia. As a result of this examination (which need not be concerned with the curvature of the eye which is a consideration in fitting many contact lenses), a lens prescription is provided. With this lens prescription, a specific holographic lens or lenses are created on a film of thin material. The film of thin material carrying the holographic lens or lenses is then divided into a plurality of particles, each of which carries at least one complete holographic lens or hologram. Alternatively, each of a plurality of particles can be processed to place the desired holographic lens on the individual particle. In any event, the plurality of particles are suitable to be placed in proximity to the outer surface of the cornea of the individual patient's eye or eyes to at least partially correct the specific effect of ametropia diagnosed by the examination.

In order to obtain an increased degree of correction of the effect of ametropia in the mammalian eye, it is preferred that the plurality of particles be adapted to be oriented when located in proximity to the outer surface of the cornea. This orientation is particularly useful when the particles are oriented relative to the light entering the mammalian eye. Thus, in a very useful embodiment, the plurality of particles is oriented such that the light entering the eye is directly diffracted by the complete hologram carried by each of the particles.

Orienting the plurality of particles in proximity to the cornea may be at least facilitated by one or more different techniques. For example, the plurality of particles can carry a charge sufficient to at least facilitate this orientation. To illustrate, since the cornea itself has a net positive charge, by producing the plurality of particles to have back sides, that is the side opposite from the holographic lens or hologram, with negative charges, the particles orient themselves with the back side of the particles facing the cornea. This provides an orientation in which the light entering the eye directly impacts on and is diffracted by the holographic lens on the front sides of the particles. This charging of the plurality of particles can occur, for example, before, during or after the formation of the thin film of material carrying the complete holographic lens or hologram.

In another embodiment, the plurality of particles can be cut from the film of thin material so as to have a shape which is effective to at least facilitate the orientation of the plurality of particles in proximity to the cornea. For example, such particles may be shaped so as to have a definitive front side or surface (defined as being the side on which the holographic lens is located) and a definitive back side (defined as the side opposite the front side). Thus, by orienting the particles so that the back sides of the particles face the cornea, for example, using the charge technique described above, the plurality of particles can be more effectively oriented, thus allowing for a greater degree of correction of the effect of ametropia in the eye. Other shapes may be useful in orienting the plurality of particles in proximity to the cornea of the eye. For example, the particles may be shaped to be bottom heavy to at least facilitate the angular orientation of the particles in proximity to the cornea of the eye. Also, the combination of particle shape and particle charge may be used to at least facilitate orientation of the particles in proximity to the cornea of the eye.

The present particles are preferably coated or otherwise treated to protect the holograms carried by the particles from the environment, for example, in the eye. To illustrate, proteins present in the tear fluid in the eye may accumulate on the particles reducing the effectiveness of the holographic lenses. In one embodiment, the particles are coated with another polymeric material, such as an optically clear silicone polymer, to protect the holographic lenses carried by the particles from direct contact with the tear fluid in the eye.

Although the particles may be used without any carrier, it is much preferred that the present compositions include an additional component in an amount effective to act as a carrier for the plurality of particles. Such additional components provide for easier introduction or placement of the plurality of particles in proximity to the cornea. Also, the concentration of the plurality of particles placed on (or in) the eye is more easily controlled using a carrier component.

In one embodiment, the particles are included in a slow release form, for example, in an insert which is placed below the lower lid of the eye. Over time, this insert releases the particles to at least partially correct an effect of ametropia in the eye. In this embodiment, the particles are preferably carried by an ophthalmically acceptable solid material, preferably a polymeric material, for example, polyvinyl alcohol or polyvinyl pyrrolidone, which slowly dissolves after being contacted with the tear fluid in the eye, thereby releasing the particles into the eye.

In another embodiment, the particles are included in a composition in which the additional component comprises a liquid, more preferably, an aqueous-based liquid, which is ophthalmically acceptable. This liquid form of the present compositions is preferably introduced to the eye in the form of a drop, such as an eye drop. This liquid form of the present compositions may be considered a "liquid contact lens".

The slow release and liquid forms of the present compositions may be used alone or in combination.

One particularly useful ophthalmically acceptable liquid carrier is water, such as purified water, sterilized water or preserved water. The additional component or carrier is preferably substantially isotonic.

Further, one or more other components may be included in the carrier or additional component to impart or provide at least one beneficial or desired property to the compositions. Such additional components may be selected from components which are conventionally used in one or more contact lens care compositions. Examples of such other components include buffers, tonicity agents, corneal nutrient agents and the like. Such other components are each included in the present compositions in an amount effective to impart or provide the beneficial or desired property to the compositions. For example, such additional components may be included in the present compositions in amounts similar to the amounts of such components used in conventional in-the-eye contact lens care products.

Examples of suitable ophthalmically acceptable buffer components include acetate buffers, citrate buffers, phosphate buffers, borate buffers and the like and mixtures thereof. Useful tonicity adjusters include, but are not limited to, sodium chloride, potassium chloride, mannitol, dextrose, glycerine, propylene glycol and the like and mixtures thereof. Suitable corneal nutrient agents include, but are not limited to, dextrose, lactose, glutaric acid, lactic acid, other ophthalmically acceptable carbohydrates and carbohydrate derivatives, glutamine, glutamic acid, other ophthalmically acceptable amino acids and the like and mixtures thereof.

In a particularly useful embodiment, the additional component further includes a maintenance component in an amount effective to maintain the plurality of particles in proximity to the outer surface of the cornea, for example, for a longer period of time, relative to a substantially identical composition without the maintenance component. In general, the use of a liquid carrier in combination with the present plurality of particles is administered or placed in proximity to the cornea of the eye by administering drops of the liquid dispersion of the particles into the eye. Over time, the tear film present in the eye causes the particles to be removed from the eye, thus reducing the correction caused by the presence of the particles in the eye. In order to achieve the desired degree of correction, additional particles may be introduced into the eye, for example, by applying additional drops of dispersion into the eye. In order to reduce the frequency of applying additional drops to the eye, the maintenance component is provided and is preferably effective to reduce the effectiveness of the tear film in removing the particles from the eye. This maintenance component preferably is present in an amount so that at least one of the viscosity and surface tension of the composition is increased relative to the corresponding property or properties of the tear fluid present in the mammalian eye into which the composition is to be placed. Increased viscosity and/or surface tension has been found to be effective to prolong the presence of the particles in proximity to the cornea of the eye.

The maintenance component is preferably selected from contact lens wetting agents, ophthalmically acceptable surfactants, ophthalmically acceptable viscosity builders, contact lens conditioning agents and mixtures thereof. Particularly useful maintenance components include polyvinyl alcohol, polyoxamers, polyvinyl pyrrolidone, ophthalmically acceptable cellulose derivatives, propylene glycol alginate, xanthan gum, alkyl polyglyosides and the like and mixtures thereof.

A particularly useful additional or carrier component are artificial tear formulations, for example, such as that sold by Allergan, Inc. under the trademark LIQUIFILM TEARS®.

The concentration of the plurality of particles in the present compositions may vary over a broad range, for example, depending on the particular application involved and the particular form of the composition. For example, if an insert is to be employed, the particles may comprise as much as 70% by weight or 80% by weight or more of the insert. However, if the composition is to include a liquid carrier, it is preferred that the additional component be present in a major amount, that is at least about 50%, or at least about 70% or at least about 80% or more by weight of the composition. The concentration of the particles in the composition is not a critical feature of the present invention provided that the concentration chosen is effective to provide the desired degree of correction of an effect of ametropia, while, at the same time, having substantially no detrimental effect on the eye into which the composition is placed or on the human or animal in whose eye the composition is placed.

In general, the present compositions may be employed in the methods for at least partially correcting an effect of ametropia in a mammalian eye described herein.

Such methods comprise placing in proximity to the outer surface of the cornea of a mammalian eye a plurality of particles each of which carries a complete hologram in an amount effective to at least partially correct an effect of ametropia in the eye.

The present methods for correcting an effective ametropia may involve using the insert form of the present compositions and/or the liquid form of the present compositions.

The present methods preferably include repeating the placing step at least once, for example, at least once every about 15 or about 30 minutes to about 6 hours or about 24 hours or longer to maintain the desired correction.

The present plurality of particles may be produced by methods which comprise forming a thin film of material carrying one or more complete holograms, each of which complete holograms holds all the information needed to at least partially correct an effect of ametropia in a mammalian eye. The thin film of material having the complete hologram or holograms is divided into a plurality of particles so that each of the plurality of particles carries at least one, and preferably only one, complete hologram.

Forming holographic lenses can be accomplished using techniques which are well known in the art. See, for example, Georgaras et al U.S. Pat. No. 5,235,441 and Freeman U.S. Pat. No. 4,641,934, the disclosure of each of which is incorporated in its entirety herein by reference.

Dividing the thin film carrying the holographic lens or lenses can be accomplished using techniques which are well known in the art. For example, the thin film of material can be cut, shredded, or otherwise divided into the desired plurality of particles.

In one particularly useful embodiment, before or after the holographic lens or lenses are provided to the thin film of material, the side of the thin film of material opposite from the holographic image is provided with a negative charge. The thin film of material is then divided into a plurality of particles having a definite front side including the hologram and a definite back side which is the side opposing the front side. This is particularly useful since the cornea has a positive charge. Thus, when the plurality of particles is placed in proximity to the cornea, the negatively charged back side of the particles orient themselves to face the positively charged cornea. This orientation allows light to directly impact the holograms on the front sides of the particles before passing to the retina of the eye. This orientation is very effective in providing correction of an effect of ametropia in the eye.

The following non-limiting Examples illustrate certain aspects of the present invention.

EXAMPLE 1

A film of polymethylmethacrylate (PMMA) having a thickness of about 10 to about 100 microns is provided. Using a conventional technique, for example, a conventional laser technique, a +2 diopter holographic lens is applied to the front side of the film.

After the holographic lens is applied, the opposing or back side of the film is conventionally treated to cause the back side to be negatively charged. Alternatively, the PMMA film can be provided with its back side negatively charged or it can be treated prior to the holographic lens being applied to cause the back side to be negatively charged. In any event, the back side of the PMMA film carrying the +2 diopter holographic lens has a back side which has a substantially uniformly distributed negative charge.

This film is then divided, for example, shredded, into PMMA particles with substantially rectangular front sides and back sides, having lengths and widths in the range of about 10 microns to about 150 microns. Alternatively, the film is divided into the particles using a photo-resist technique similar to such techniques which are conventional and well known in the production of semi-conductors. The front side of each of the particles carries a complete hologram having information necessary for a +2 diopter holographic lens. The back side of each of these particles has sufficient negative charge to be attracted to a positively charged cornea when placed in proximity to the outer surface of such a cornea.

EXAMPLE 2

A quantity of the particles produced in Example 1 is combined with ophthalmically acceptable polyvinyl alcohol to form an eye insert including about 30% to about 70% by weight of solid polyvinyl alcohol and about 30% to about 70% by weight of the particles.

EXAMPLE 3

The eye insert produced in Example 2 is placed under the lower eye lid of an eye which has an effect of ametropia that can be corrected by the holographic lens carried by each of the particles. The polyvinyl alcohol in the eye insert slowly dissolves in the tear fluid in the eye and the particles are slowly released from the eye insert and at least some of the particles move into proximity to the outer surface of the cornea of the eye. Over a period of time, for example, on the order of about 24 hours, the effect of ametropia experienced by the eye is at least partially corrected.

EXAMPLE 4

A quantity of the particles produced in Example 1 is combined with an artificial tear formulation, for example, the product sold by Allergan, Inc., under the trademark LIQUIFILM TEARS®. A liquid composition containing the particles dispersed within results.

EXAMPLE 5

A drop of the composition produced in Example 4 is applied to an eye which has an effect of ametropia that can be corrected by the holographic lens carried by each of the particles. At least some of the particles move in proximity to the outer corneal surface of the eye. Every 30 minutes to 1 hour thereafter, an additional drop of the composition is applied to the eye. Over a period of time of 12 hours, the effect of ametropia experienced by the eye is at least partially corrected.

EXAMPLE 6

Example 5 is repeated except that an eye insert produced as in Example 2 is placed under the lower eye lid of the eye immediately prior to the first drop of the composition produced in Example 4 being applied to the eye. Over a period of time of 12 hours, the effect of ametropia experienced by the eye is at least partially corrected. In this embodiment, the drops need to be added to the eye every 2 to 4 hours.

EXAMPLE 7

A film of polymethylmethacrylate (PMMA) having a thickness of about 10 to about 100 microns is provided. Using a conventional technique, for example, a conventional laser technique, a plurality of individual +2 diopter holographic lenses are applied to individual circular areas (having diameters in the range of about 10 microns to about 150 microns) of the front side of the film. Each of the holographic lenses has a circular configuration.

After the holographic lenses are applied, the opposing or back side of the film is conventionally treated to cause the back side to be negatively charged. Alternatively, the PMMA film can be provided with its back side negatively charged or it can be treated prior to the holographic lenses being applied to cause the back side to be negatively charged. In any event, the back side of the PMMA film carrying the +2 diopter holographic lenses has a back side which has a substantially uniformly distributed negative charge.

This film is then divided, for example, shredded, into PMMA particles with substantially rectangular front sides and back sides, having lengths and widths in the range of about 50 microns to about 150 microns. Alternatively, the film is divided into the particles using a photo-resist technique similar to such techniques which are conventional and well known in the production of semi-conductors. The front side of each of the particles carries a complete hologram having all the information necessary for a +2 diopter holographic lens. The back side of each of these particles has sufficient negative charge to be attracted to a positively charged cornea when placed in proximity to the outer surface of such a cornea.

EXAMPLE 8

A quantity of the particles produced in Example 7 is combined with ophthalmically acceptable polyvinyl alcohol to form an eye insert including about 30% to about 70% by weight of solid polyvinyl alcohol and about 30% to about 70% by weight of the particles.

EXAMPLE 9

The eye insert produced in Example 8 is placed under the lower eye lid of an eye which has an effect of ametropia that can be corrected by the holographic lens carried by each of the particles. The polyvinyl alcohol in the eye insert slowly dissolves in the tear fluid in the eye and the particles are slowly released from the eye insert and at least some of the particles move into proximity to the outer surface of the cornea of the eye. Over a period of time, for example, on the order of about 24 hours, the effect of ametropia experienced by the eye is at least partially corrected.

EXAMPLE 10

A quantity of the particles produced in Example 7 is combined with an artificial tear formulation, for example, the product sold by Allergan, Inc., under the trademark LIQUIFILM TEARS®. A liquid composition containing the particles dispersed within results.

EXAMPLE 11

A drop of the composition produced in Example 10 is applied to an eye which has an effect of ametropia that can be corrected by the holographic lens carried by each of the particles. At least some of the particles move in proximity to the outer corneal surface of the eye. Every 30 minutes to 1 hour thereafter, an additional drop of the composition is applied to the eye. Over a period of time of 12 hours, the effect of ametropia experienced by the eye is at least partially corrected.

EXAMPLE 12

Example 11 is repeated except that an eye insert produced as in Example 8 is placed under the lower eye lid of the eye immediately prior to the first drop of the composition produced in Example 10 being applied to the eye. Over a period of time of 12 hours, the effect of ametropia experienced by the eye is at least partially corrected. In this embodiment, the drops need to be added to the eye every 2 to 4 hours.

The present systems for correcting an effect of ametropia in the eye are very easy and convenient to use. In addition, such systems free the user from having to care for contact lenses. The present compositions are easily and effectively customized (based on the particular effect of ametropia to be corrected) to meet the requirements of the individual user.

While this invention has been described with respect to various specific examples and embodiments, it is to be understood that the invention is not limited thereto and that it can be variously practiced with the scope of the following claims.

What is claimed is:

1. A composition comprising a plurality of particles sized and adapted to be placed in proximity to the outer surface of the cornea of a mammalian eye to at least partially correct an effect of ametropia in the mammalian eye, each of said plurality of particles carrying a complete hologram which holds all the information needed to at least partially correct an effect of ametropia in the mammalian eye.

2. The composition of claim 1 wherein said plurality of particles are adapted to be oriented when located in proximity to the outer surface of the cornea of the mammalian eye to increase the degree of correction of the effect of ametropia in the mammalian eye.

3. The composition of claim 1 which further comprises an additional component in an amount effective to act as a carrier for said plurality of particles.

4. A composition comprising a plurality of particles which are solid and are sized and adapted to be placed in proximity to the outer surface of the cornea of a mammalian eye to at least partially correct an effect of ametropia in the mammalian eye.

5. The composition of claim 4 wherein each of said plurality of particles carries a complete hologram which holds all the information needed to at least partially correct an effect of ametropia in the mammalian eye.

6. The composition of claim 4 wherein each of said plurality of particles carries a complete hologram effective to at least partially correct an effect of ametropia in the mammalian eye, and said plurality of particles are sized and adapted to be substantially non-irritating to the mammalian eye when located in proximity to the outer surface of the cornea of the mammalian eye.

7. The composition of claim 4 wherein said plurality of particles are sized and adapted to be substantially non-detectable to the feeling sense of the human or animal in whose eye said plurality of particles are placed.

8. The composition of claim 4 wherein each of said plurality of particles has a maximum transverse dimension in the range of about 10 microns or less to about 1000 microns or more.

9. The composition of claim 4 wherein said plurality of particles are adapted to be oriented when located in proximity to the outer surface of the cornea of the mammalian eye to increase the degree of correction of the effect of ametropia in the mammalian eye.

10. The composition of claim 9 wherein said orientation is relative to the light entering the mammalian eye.

11. The composition of claim 9 wherein each of said plurality of particles carries a charge sufficient to at least facilitate said orientation.

12. The composition of claim 9 wherein each of said particles has a shape which is effective to at least facilitate said orientation.

13. The composition of claim 4 which further comprises an additional component in an amount effective to act as a carrier for said plurality of particles.

14. The composition of claim 13 wherein said additional component is an ophthalmically acceptable solid which solubilizes over a period of time after being in contact with tear fluid present in the mammalian eye into which said composition is placed.

15. The composition of claim 13 wherein said additional component is an aqueous-based liquid and is ophthalmically acceptable.

16. The composition of claim 13 wherein said additional component includes a maintenance component in an amount effective to maintain said plurality of particles in proximity to the outer surface of the cornea of the mammalian eye relative to a substantially identical composition without said maintenance component.

17. The composition of claim 16 wherein said maintenance component is present in an amount so that at least one of the viscosity and surface tension of said composition is increased relative to the corresponding property or properties of the tear fluid present in the mammalian eye into which said composition is to be placed.

18. The composition of claim 16 wherein said maintenance component is selected from the group consisting of contact lens wetting agents, ophthalmically acceptable surfactants, ophthalmically acceptable viscosity builders, contact lens conditioning agents and mixtures thereof.

19. The composition of claim 16 wherein said maintenance component is selected from the group consisting of polyvinyl alcohol, polyoxamers, polyvinyl pyrrolidone, ophthalmically acceptable cellulose derivatives, propylene glycol alginate, xanthan gum, alkyl polyglycosides and mixtures thereof.

20. A method of producing a plurality of particles useful to at least partially correct an effect of ametropia in a mammalian eye, which method comprises:

forming a thin film of material carrying a complete hologram, said complete hologram holding all the information needed to at least partially correct an effect of ametropia in a mammalian eye; and dividing said thin film of material having said complete hologram into a plurality of particles so that each of said plurality of particles carries said complete hologram.

21. The method of claim 20 wherein before, during or after said forming step a sufficient charge is selectively placed on one portion of said thin film of material so that each of said plurality of particles is charged to at least facilitate orienting said plurality of particles when said plurality of particles are in proximity to the outer surface of a cornea of a mammalian eye, and said dividing step is effective to yield a plurality of particles each of which has a shape effective to at least facilitate orienting said plurality of particles when said plurality of particles are in proximity to the outer surface of a cornea of a mammalian eye.

22. A method of producing a plurality of particles useful to at least partially correct an effect of ametropia in a mammalian eye, which method comprises:

forming a thin film carrying a plurality of complete holograms each of which holding all the information needed to at least partially correct an effect of ametropia in a mammalian eye; and dividing said thin film of material having said plurality of complete holograms into a plurality of particles so that each of said plurality of particles carries at least one of said plurality of complete holograms.

23. The method of claim 22 wherein each of said plurality of particles has a maximum transverse dimension of about 1000 microns or less.

24. The method of claim 22 wherein before, during or after said forming step a sufficient charge is selectively placed on one portion of said thin film of material so that each of said plurality of particles is charged to at least facilitate orienting said plurality of particles when said plurality of particles are in proximity to the outer surface of a cornea of a mammalian eye, and said dividing step is effective to yield a plurality of particles each of which has a shape effective to at least facilitate orienting said plurality of particles when said plurality of particles are in proximity to the outer surface of a cornea of a mammalian eye.

\* \* \* \* \*